United States Patent [19]
Bercu et al.

[11] Patent Number: 5,246,920
[45] Date of Patent: Sep. 21, 1993

[54] TREATMENT OF HYPERPROLACTINEMIA

[75] Inventors: Barry B. Bercu, Tampa; Richard F. Walker, Indian Rocks, both of Fla.

[73] Assignee: University of South Florida, Tampa, Fla.

[21] Appl. No.: 898,523

[22] Filed: Jun. 15, 1992

[51] Int. Cl.$^5$ ...................... A61K 37/02; A61K 37/24
[52] U.S. Cl. ........................................ 514/12; 514/17
[58] Field of Search .................................. 514/12, 17

[56] References Cited

U.S. PATENT DOCUMENTS

| | | | |
|---|---|---|---|
| Re. 33,699 | 9/1991 | Drengler | 424/422 |
| 4,517,181 | 5/1985 | Ling et al. | 514/12 |
| 4,518,586 | 5/1985 | Rivier et al. | 514/12 |
| 4,528,190 | 7/1985 | Vale, Jr. | 514/12 |
| 4,529,595 | 7/1985 | Rivier et al. | 514/12 |
| 4,562,175 | 12/1985 | Chang et al. | 514/12 |
| 4,563,352 | 1/1986 | Rivier et al. | 514/12 |
| 4,585,756 | 4/1986 | Brazeau, Jr. et al. | 514/12 |
| 4,595,676 | 6/1986 | Spiess et al. | 514/12 |
| 4,605,643 | 8/1986 | Bohlen et al. | 514/12 |
| 4,610,976 | 9/1986 | Bohlen et al. | 514/12 |
| 4,617,149 | 10/1986 | DiMarchi et al. | 530/324 |
| 4,622,312 | 11/1986 | Felix et al. | 514/12 |
| 4,626,523 | 12/1986 | Vale, Jr. et al. | 514/12 |
| 4,649,131 | 3/1987 | Felix et al. | 514/12 |
| 4,657,932 | 4/1987 | Martin et al. | 514/665 |
| 4,710,382 | 12/1987 | Recker | 514/12 |
| 4,774,319 | 9/1988 | Ono et al. | 530/324 |

OTHER PUBLICATIONS

Blake et al. J. Endocrinol vol. 129 (1) pp. 11-20 (1991).
Edwards et al. J. Endocrinol. vol. 121(1) pp. 31-36 (1989).
Yap et al. Am. J. Obstet. Gynocol. vol. 163(2) pp. 477-478.
Bercu et al. Endocrinol. vol. 130(5) pp. 2579-2586 (1992).
Giush et al. Clin. Endocrinol. vol. 30(3) pp. 315-321 (Mar. 1989).
Walhor et al. Life Sci. vol. 47(1) (1990) pp. 29-36.
Diequez et al. Neuroendocrinology, vol. 52 (suppl) (1990) p. 76.
Asa et al. J. Clin. Endocrinol. & Metabol. vol. 75(1) 1992 pp. 68-75.
Venetikon et al. Acta Endocrinol. vol. 116(2) pp. 287-292 (1987).
Bercu et al. Endocrinology vol. 131(6) pp. 2800-2804 (1992).
Bowers et al., Endocrinol. 124: 2791-2798 (1989).
Cheng et al., Endocrinol 124:2791-2798 (1989).
Momany et al., Endocrinol. 114:1531 (1984).
Walker et al., Life Sciences 49:1499-1504 (1991).
Rudman et al., New Eng. Jour. Med. 323:1-6 (1990).

*Primary Examiner*—Michael G. Wityshyn
*Assistant Examiner*—Choon Koh
*Attorney, Agent, or Firm*—Reising, Ethington, Barnard, Perry & Milton

[57] ABSTRACT

A method for the treatment of hypersecretion of prolactin in a patient which comprises co-administration of an effective amount of a growth hormone releasing compound and GHRP-6 or an analog thereof.

8 Claims, No Drawings

TREATMENT OF HYPERPROLACTINEMIA

TECHNICAL FIELD

The present invention is directed to a method for treating hyperprolactinemia which is a condition resulting in hypersecretion of prolactin.

BACKGROUND OF THE INVENTION

During aging, or in certain pathological conditions, reduction of brain catecholamines causes the regulatory processes controlling pituitary hormone secretion to decay. Of concern in this invention are reciprocal changes in growth hormone (GH) which is reduced and prolactin which is increased. Catecholamines are somatotrophic because they provide primary stimuli to GHRH neurosecretory neurons which in turn stimulate the pituitary gland to release GH. In contrast, catecholamines directly suppress prolactin secretion by activating dopamine receptors on lactotrophs within the pituitary gland. Because of this dual action, age or pathology-related decreases in brain catecholamine concentrations or availability reduce GH secretion and increase prolactin secretion. Ultimately, lactotroph hypertrophy and/or hyperplasia lead to the development of prolactin secreting adenomas We have found that chronic stimulation of the somatotroph population by daily co-administration of a growth hormone releasing compound and GHRP-6 or analog thereof prevented lactotroph hypersecretion, proliferation and adenoma formation and caused regression of pre-existing tumors. Since prolactin secreting adenomas are treated clinically by surgery or by administration of dopamine agonists, our invention provides a new therapeutic alternative to the treatment of hyperprolactinemia and certain pathological changes in pituitary structure, i.e., the pharmacological stimulation of somatotrophs to reduce lactotroph hyperactivity and regression of lactotroph adenomas.

SUMMARY OF THE INVENTION

The present invention provides a method for the treatment of hypersecretion of prolactin and/or maladaptive changes in a patient by co-administering to said patient, a growth hormone releasing compound and the hexapeptide GHRP-6 or an analog thereof. The present invention provides a method for treating lactotroph hypertrophy, lactotroph hyperplasia and pituitary lactotroph adenomas, as well as increased prolactin secretion resulting from dysmorphic changes.

A preferred embodiment of the present invention is the co-administration of a growth hormone releasing compound and GHRP-6.

The most preferred growth hormone releasing compound for use in practicing the present invention is growth hormone releasing hormone (GHRH) which is also known as growth hormone releasing factor (GHRF or GRF). Each of GHRH (1-44), GHRH (1-40) and GHRH (1-29) are particularly useful in practicing the present invention in combination with GHRP-6 and analogs thereof.

DETAILED DESCRIPTION OF THE INVENTION

Hyperprolactinemia is a condition involving increased levels of prolactin in the blood of a patient. In women hyperprolactinemia is associated with amenorrhea, i.e., the abnormal stoppage of menses unrelated to aging and galactorrhea, i.e., the spontaneous flow of milk. In men hyperprolactinemia can cause hypogonadism and impotence. Individuals with hyperprolactinemia in most instances experience infertility and if hyperprolactinemia is associated with enlargement of the pituitary gland due to lactotroph hypertrophy, hyperplasia or adenoma formation, these individuals also may suffer from a persistent headache and vision disturbances. These specific manifestations of the condition permit a physician to diagnose the patient readily.

Hyperprolactinemia or the hypersecretion of prolactin can be the result of a microadenoma in the anterior pituitary, i.e., a neoplastic change in lactotrophs, or can be due to hypersecretion of lactotrophs, i.e., the cells which secrete prolactin, as the result of increased lactotroph activity characterized by hypertrophy, or as the result of lactotroph hyperplasia characterized by hyperproliferation. Patients having hyperprolactinemia or diagnosed by some other method as having dysmorphic and/or dysfunctional changes in pituitary lactotroph-/somatotroph populations will be treated, according to the present invention, with a combination of peptides to pharmacologically stimulate the somatotrophs. In particular the patient is co-administered a growth hormone releasing compound and GHRP-6 or an analog thereof.

The term growth hormone releasing compound means any compound which is known to induce secretion of GH and includes GHRH (1-44) and analogs GHRH (1-40) and GHRH (1-29). There are numerous growth hormone releasing compounds known in the art and any of these compounds will be useful in practicing the present invention. U.S. Pat. No. 4,622,312 provides an excellent description of GHRH and analogs thereof which can be used in the presently claimed invention. U.S. Pat. No. Re. 33,699 provides a summary of patents which teach growth hormone releasing compounds. The growth hormone releasing compounds taught in each of the following U.S. patents are suitable for use in the method of the present invention:

| COUNTRY | U.S. Pat. No. | COLUMN | LINE |
|---|---|---|---|
| U.S. | RE 33,699 | 1-4 | |
| U S. | 4,517,181 | 2 | |
| U.S. | 4,518,586 | 1-4 | |
| U.S. | 4,528,190 | 1-2 | |
| U.S. | 4,529,595 | 1-4 | |
| U.S. | 4,562,175 | 1-2 | |
| U.S. | 4,563,352 | 1-4 | |
| U.S. | 4,585,756 | 1-2 | |
| U.S. | 4,595,676 | 1-2 | |
| U.S. | 4,605,643 | 1-2 | |
| U.S. | 4,610,976 | 1-2 | |
| U.S. | 4,617,149 | 1-4 | |
| U.S. | 4,622,312 | 1-4 | 10 |
| U.S. | 4,626,523 | 1-2 | |
| U.S. | 4,649,131 | 1-4 | 19 |
| U.S. | 4,710,382 | 1-2 | |
| U.S. | 4,774,319 | 1 | |

The above U.S. patents, and in particular the portions indicated above by column and line number, are incorporated herein by reference as teaching growth hormone releasing compounds that are useful in the practice of the presently claimed invention.

The term GHRP-6 and analogs thereof means GHRP and any peptide compound that releases GH by the same cellular mechanism. GHRP-6 is the hexapeptide His-D-Trp-Ala-Trp-D-Phe-Lys-NH$_2$ and is believed to act directly on the pituitary to cause release of GH. In addition to GHRP-6, the pentapeptide Tyr-D-Trp-Gly-Phe-Met-NH$_2$ [K. Cheng et al., Endocrinol. 124, 2791-2798 (1989)], is a useful analog in the release of GH. Other compounds considered analogs of GHRP-6 for purposes of the present invention have been reported. For example, C.Y. Bowers et al., Endocrinol. 106, 663 (1980) teaches in addition to Tyr-D-Trp-Gly-Phe-Met-NH$_2$, compounds Tyr-D-Phe-Gly-Phe-Met-NH$_2$ and Trp-D-Phe-Pro-Phe-Met-COOH as being useful in the release of growth hormone; and GHRP-1 having the formula Ala-His-D-$\beta$-Nal-Ala-Trp-D-Phe-Lys-NH$_2$ disclosed in Abstract 521, 74th Annual Meeting of the Endocrine Society, June 24-27, 1992, p. 182, San Antonio, Tex. is also useful in the release growth hormone. Also, F. A. Momany et al., Endocrinol. 108, 31 (1981) teaches the following compounds as being useful in the release of growth hormone: Try-Ala-D-Trp-Phe-Met-NH$_2$; Tyr-D-Trp-D-Trp-Phe-Met-NH$_2$; Tyr-D-Trp-D-Trp-Phe-NH$_2$; Tyr-D-Trp-D-Trp-Phe-COOH; and D-Trp-D-Trp-Phe-NH2. Additionally, F. A. Momany et al., Endocrinol. 114, 1531 (1984) teaches the following compounds as being useful in the release of growth hormone: His-D-Trp-Ala-Trp-D-Phe-NH$_2$; His-D-Trp-Ala-Trp-D-Phe-Lys-NH$_2$; Tyr-D-Trp-Ala-Trp-D-Phe-NH$_2$; His-D-Trp-Ala-Trp-D-Phe-Arg-NH$_2$; and His-D-Trp-Ala-Trp-D-Phe-Lys-COOH. All of these compounds are useful in practicing the present invention when co-administered with a growth hormone releasing compound as described herein, however, these peptides should not be considered as being exhaustive of the GHRP-6 analogs useful in practicing the present invention.

In the method of the present invention the growth hormone releasing compound and the GHRP-6 or analog thereof can be administered in various ways. It should be noted that the growth hormone releasing compound and GHRP-6 or analog thereof each can be administered as the compound or as pharmaceutically acceptable salts of the compounds and can be administered alone or in combination with pharmaceutically acceptable carriers. The compounds can be administered orally or parenterally including intravenous, intramuscularly, intraperitoneally, intranasal and subcutaneous administration. Implant of the compounds are also useful. The patient being treated is a warm-blooded animal and, in particular, mammals including man.

When administering the growth hormone releasing compound and GHRP-6 or analog thereof parenterally, the pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters such as isopropyl myristate may also be used as solvent systems for compound compositions. Additionally, various additives which enhance the stability, sterility, and isotonicity of the compositions including antimicrobial preservatives, antioxidants, chelating agents, and buffers can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. Any vehicle, diluent, or additive used would, however, have to be compatible with the compounds according to the present invention.

Sterile injectable solutions can be prepared by incorporating the compounds utilized in practicing the present invention in the required amount of the appropriate solvent with various of the other ingredients, as desired.

The growth hormone releasing compound and GHRP-6 or analog thereof can be administered to the patient in an injectable formulation containing any compatible carrier such as various vehicle, adjuvants, additives, and diluents or, the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks. Examples of well known implants and modules useful in the present invention include: U.S. Pat. NO. 4,487,603 which discloses an implantable micro-infusion pump for dispensing medication at a controlled rate. U.S. Pat. No. 4,486,194 discloses a therapeutic device for administering medicants through the skin. U.S. Pat. No. 4,447,233 discloses a medication infusion pump for delivering medication at a precise infusion rate. U.S. Pat. No. 4,447,224 discloses a variable flow implantable infusion apparatus for continuous drug delivery. U.S. Pat. No. 4,439,196 discloses an osmotic drug delivery system having multi-chamber compartments. U.S. Pat. No. 4,475,196 discloses an osmotic drug delivery system. These patents are incorporated herein by reference. Many other such implants, delivery systems, and modules are well known to those skilled in the art.

The growth hormone releasing compound and GHRP-6 or analog thereof utilized in the present invention can be administered orally to the patient. Conventional methods such as administering the compounds in tablets, suspensions, solutions, emulsions, capsules, powders, syrups and the like are usable. Known techniques which deliver the peptide orally and retain the biological activity of the peptide are preferred.

According to the present invention, one composition for stimulating the release of GH comprises a pharmaceutically acceptable carrier and an amount of the growth hormone releasing compound and GHRP-6 or analog thereof sufficient to stimulate the release of GH admixed with the carrier.

In administering the compounds utilized in the present invention it is contemplated that the patient would be co-administered the growth hormone releasing compound and GHRP-6 or analog thereof by intravenous injection initially. The patient would be monitored to detect improvement in the outward manifestations, i.e., hyperprolactinemia. The patients prolactin levels would be measured to determine when they approach or reach normal levels after which the patients will be maintained with daily co-administration of the compounds preferably in an oral dosage form, although other forms of administration, as indicated above, can be used. Magnetic resonance imaging can be utilized to monitor any change in size of pituitary adenomas. Dose and duration of treatment will be determined for each patient depending upon the degree and rate of hyperprolactinemia reduction and/or reduction in pituitary size.

The quantity of growth hormone releasing compound to be administered will vary for the patient being treated and will vary from about 100 ng/kg of body weight to 100 mg/kg of body weight per day and more preferably will be from 10 μg/kg to 10 mg/kg per day. The quantity of GHRP-6 or analog thereof to be administered will vary from about 100 ng/kg to 1 mg/kg of body weight per day.

Efficacy of the peptide combination will be determined by characterizing growth hormone secretory profiles after co-administration of the peptides at selected intervals during the course of treatment.

The following study and test results illustrate the utility of the present invention. Natural growth hormone releasing hormone (GHRH) and xenobiotic GH releasing hexapeptide (GHRP-6) were co-administered to aged (24 month old) Fischer 344 female rats for 60 consecutive days. The quantity of GHRH and GHRP-6 subcutaneously administered each day was 3 μg/kg and 300 μg/kg, respectively. Repeated co-administration of the GH secretagogues was investigated because the results of a pilot study showed that paradoxical, robust secretion of growth hormone (GH) occurred in old rats, despite the fact that they had low pituitary GH reserves and were relatively insensitive to the individually administered peptides [Walker et al., Life Sciences 49, 1499–1504 (1991)]. Since exogenous GH had beneficial effects in a clinical study involving men > 60 years of age [Rudman et al., New Eng. J. Med. 323, 1–6 (1990)], it was of interest to determine whether the pituitaries of old animals could sustain GH secretion in response to repeated stimulation, and whether endogenous GH was also efficacious in reversing some of the maladaptive changes associated with advanced age. One of the findings included a statistically significant reduction in mean pituitary weight that was associated with a lack of macroscopic adenomas and reduced plasma prolactin concentrations in the treated, old rats. The data were quite unexpected since hyperprolactinemia associated with lactotroph hypertrophy and/or hyperplasia are pathological concommittants of aging that have not heretofore been associated with changes in somatotroph activity. The lack of tumors in the treated rats was biologically significant since they occur in nearly all Fischer rats greater than 24 months of age.

The results of this study are summarized in the following Table.

TABLE

Effects of chronic co-administration of GHRH and GHRP-6 on selected endocrine functions in rats with hyperprolactinemia, pituitary hypertrophy and pituitary lactotroph adenomas.

| ENDOCRINE PARAMETER | YOUNG (SALINE) | OLD (SALINE) | OLD (GHRH/GHRP-6) |
|---|---|---|---|
| Pituitary Weight (mg ± sem) | 11.3 ± 3.1 | 58 ± 11.1* | 15.6 ± 6.9 |
| Pituitary Tumor Incidence (%) | 0 | 83* | 17 |
| Plasma GH (ng/ml) | 683 ± 213 | 956 ± 225* | 402 ± 127 |
| Pituitary GH (μg/mg wet wgt) | 248 ± 35 | 39 ± 15* | 275 ± 38 |
| Plasma IGF-1 (ng/ml) | 839 ± 31 | 542 ± 32* | 780 ± 24 |
| Plasma Prolactin (ng/ml) | 22 ± 9 | 375 ± 121* | 54 ± 8 |

Values represent mean ± s.e.m. for duplicate determination from six rats per group.
*Different from control ($p < 0.05$).

Tumor regression is shown by the data because of the high tumor incidence in the control population, which is typical of rats approximately 2 years of age. At 26 months of age, when the study was completed, pituitary tumors or significant pituitary hypertrophy should have affected more than 18% of the population as occurred in the rats treated with GH secretagogues. Thus, this finding provides a new treatment for hyperprolactinemia as well as pituitary lactotroph hypertrophy/hyperplasia/transformation.

The invention has been described in an illustrative manner, and it is to be understood that the terminology which has been used is intended to be in the nature of words of description rather than of limitation.

What is claimed is:

1. A method for the treatment of hyperprolactinemia in a patient in need thereof which comprises co-administering to said patient effective amounts of a growth hormone releasing compound and GHRP-6 or an analog thereof.

2. The method of claim 1 wherein the hyperprolactinemia is the result of lactotroph hypersecretion, which may be characterized by hypertrophy.

3. The method of claim 2 wherein the hyperprolactinemia is the result of lactotroph hyperplasia, which results from cell proliferation.

4. The method of claim 3 wherein the hyperprolactinemia is the result of a pituitary adenoma, which is a neoplastic change that occurs in lactotrophs.

5. The method of claim 4 wherein the growth hormone releasing compound is growth hormone releasing hormone (GHRH) (1-44), GHRH (1-40) or GHRH (1-29).

6. The method of claim 5 wherein the GHRP-6 or analog thereof is GHRP-6.

7. The method of claim 6 wherein the growth hormone releasing compound is growth hormone releasing hormone (GHRH) (1-44), GHRH (1-40) or GHRH (1-29).

8. The method of claim 7 wherein the effective amount of GHRH (1-44), GHRH (1-40) or GHRH (1-29) administered is from 100 ng/kg body weight to 100 mg/kg body weight of the patient per day and the effective amount of GHRP-6 is from 100 ng/kg body weight to 1 mg/kg body weight of the patient per day.

* * * * *